(12) United States Patent
Linton

(10) Patent No.: US 7,683,008 B2
(45) Date of Patent: Mar. 23, 2010

(54) HIGH-STRENGTH, LOW-TEMPERATURE STABLE HERBICIDAL FORMULATIONS OF 2,4-DICHLOROPHENOXY ACETIC ACID SALTS

(75) Inventor: Mark Richard Linton, Paraparaumu (NZ)

(73) Assignee: Dow AgroSciences LLC, Indianapolis, IN (US)

( * ) Notice: Subject to any disclaimer, the term of this patent is extended or adjusted under 35 U.S.C. 154(b) by 518 days.

(21) Appl. No.: 11/497,915

(22) Filed: Aug. 2, 2006

(65) Prior Publication Data

US 2008/0032892 A1 Feb. 7, 2008

(51) Int. Cl.
*A01N 39/02* (2006.01)
*A01N 39/04* (2006.01)

(52) U.S. Cl. ........................ 504/145; 504/323
(58) Field of Classification Search ............ 504/145, 504/323
See application file for complete search history.

(56) References Cited

U.S. PATENT DOCUMENTS 3,770,413 A * 11/1973 Tabor et al. ............ 504/122

\* cited by examiner

*Primary Examiner*—Alton N Pryor
(74) *Attorney, Agent, or Firm*—Craig E. Mixan

(57) ABSTRACT

This invention relates to a high-strength herbicidal formulation containing high concentrations of 2,4-D salt mixtures. The 2,4-D salt mixtures can include the DMA salt and the DMEA and/or the DEEA salt of 2,4-D. Selected combinations of the 2,4-D salt mixtures exhibit significantly greater low temperature stability at high concentrations.

3 Claims, No Drawings

HIGH-STRENGTH, LOW-TEMPERATURE STABLE HERBICIDAL FORMULATIONS OF 2,4-DICHLOROPHENOXY ACETIC ACID SALTS

BACKGROUND OF THE INVENTION

The present invention relates to herbicidal formulations of 2,4-dichlorophenoxy acetic acid (2,4-D). More particularly, the present invention concerns high-strength formulations of mixed 2,4-D salts that remain liquid at low temperature.

2,4-D is a known, effective herbicide. Various formulations are currently marketed, many of which are aqueous solutions that can be used as is or diluted prior to use. Typically the 2,4-D is provided as a salt, which exhibits sufficiently high solubility in water to provide a high-strength aqueous herbicidal formulation. A high-strength formulation is desirable for a variety of economic and environmental reasons. For example, it is desirable to provide a high-strength formulation to reduce shipping and handling costs and to reduce the amount of packaging material that must be disposed. The high-strength formulations should be stable and retain potency during storage and shipping. Furthermore, the high-strength formulation should be a clear, homogeneous liquid that is stable at ambient temperatures and should not exhibit any precipitation at temperatures as low as 0° C.

A major limitation of the dimethylamine (DMA) salt of 2,4-D is limited stability at low temperature and high concentration. For example, an aqueous formulation containing 625 grams acid equivalent per liter (gae/L) of the DMA salt of 2,4-D crystallizes at 0° C. The present invention addresses these needs and provides a wide variety of benefits and advantages.

SUMMARY OF THE INVENTION

Surprisingly, it has now been found that the low temperature solubility of a high-strength 2,4-D DMA solution can be improved by adding the dimethylethanolamine (DMEA) or diethylethanolamine (DEEA) salt of 2,4-D to the solution.

The present invention provides a herbicidal formulation comprising a mixture of DMA salt of 2,4-D with a DMEA salt or a DEEA salt of 2,4-D or a mixture thereof in a relative ratio of 2,4-D DMA salt to 2,4-D DMEA or DEEA salt of between about 55:45 to about 40:60.

In still yet another form, the present invention provides a method of treating plants with a herbicidal formulation. The formulation can be provided as described above. The formulation is typically applied as a post-emergent herbicide. The formulation can be applied as a highly concentrated solution or alternatively diluted prior to application to the plants.

DETAILED DESCRIPTION OF THE INVENTION

In general the present invention is directed to high-strength herbicidal formulations containing 2,4-D salt mixtures. The 2,4-D salt mixture comprises a combination of cations selected from dimethylethanolamine (DMEA) and/or diethylethanolamine (DEEA) cations in admixture with dimethylamine (DMA) cations. The relative amounts of the DMEA and/or DEEA to DMA salts are selected to be between about 45 and about 60 weight percent (wt %) DMEA and/or DEEA salt of 2,4-D and between about 40 and about 55 wt % DMA salt of 2,4-D.

The herbicidal formulation includes the 2,4-D salt mixture in an amount sufficient to provide the high-strength formulation. The high-strength herbicidal formulation includes at least about 625 gram acid equivalents per liter (gae/L) to about 740 gae/L based upon the 2,4-D acid equivalent of the 2,4-D salt mixture; more preferably, the high-strength herbicidal formulation includes at least about 710 gae/L to about 725 gae/L based upon the 2,4-D acid equivalent of the 2,4-D salt mixture.

Furthermore, the herbicidal formulation also does not exhibit separation or precipitation (or crystallization) of any of the components at low temperatures. For example, the high-strength formulation remains a clear solution at temperatures below about 10° C., more preferably at temperatures about 0° C.

The formulations described herein can be applied to plants in an amount sufficient to induce a herbicidal effect. For example, a formulation prepared according the present invention can be applied as an aqueous solution to plants including the plants' leaves, stems, branches, flowers and/or fruit. The herbicidal formulation can be applied in a herbicidally effective amount sufficient to inhibit plant growth or kill individual plants.

The agricultural compositions prepared according to the present invention are highly effective as a herbicide composition against a variety of weeds and can be used to control weeds in 2,4-D tolerant crops. The formulations of the present invention can be used as is or combined with other components including other agriculturally acceptable adjuvants commonly used in formulated agricultural products, such as antifoam agents and/or sequestering agents. The concentrated agricultural formulations are typically diluted in water and then applied by conventional means well known to those in the art.

For the purpose of promoting further understanding and appreciation of the present invention and its advantages, the following Examples are provided. It will be understood, however, that these Examples are illustrative and not limiting in any fashion.

The following examples are presented to illustrate the invention.

Example 1

Preparation of High-Strength 2,4-D Mixed Salt Formulations

A high-strength 2,4-D formulation was prepared containing 728 gram acid equivalent (gae) of 2,4-D per liter (L) in the form of a mixture of 45% DMA/55% DMEA by dissolving 2,4-D technical (58.8 wt %), dimethylamine (5.5 wt %) and dimethylethanolamine (13 wt %) with stirring in water (22.7 wt %) at room temperature.

Example 2

Storage Stability of High-Strength 2,4-D Mixed Salt Formulations

High-strength 2,4-D formulations were prepared containing 720 gae of 2,4-D per L according to the general procedure described in Example 1. The formulations contained varying amounts of DMA salt and DMEA salt. Storage stability results at room temperature and at 0° C. are summarized in Table I.

TABLE 1

| Percentages: | | | Storage: | |
| --- | --- | --- | --- | --- |
| DMA | DMEA | pH ("as is") | 0° C. | RT |
| 100 | 0 | 7.03 | X | C |
| 70 | 30 | 7.46 | X | C |
| 60 | 40 | 7.51 | X | C |
| 55 | 45 | 7.65 | C | C |
| 50 | 50 | 7.74 | C | C |

TABLE 1-continued

| Percentages: | | | Storage: | |
|---|---|---|---|---|
| DMA | DMEA | pH ("as is") | 0° C. | RT |
| 45 | 55 | 7.83 | C | C |
| 40 | 60 | 7.90 | C | C |
| 30 | 70 | 7.99 | X | C |
| 0 | 100 | 8.18 |  | X |

☐ not tested
X crystallized
C clear

The results in Table 1 clearly demonstrate the synergistic effect of the mixed 2,4-D salt solution on the cold temperature stability. Whereas the straight 2,4-D DMA salt crystallizes at 0° C. and the straight 2,4-D DMEA salt crystallizes even at room temperature, the mixed 2,4-D DMA/DMEA salt solution at certain ratios provides a clear solution at 0° C. free from any crystals.

What is claimed is:

1. A stable, high-strength herbicidal formulation, which remains a clear, homogeneous liquid at temperatures as low as 0° C., comprising a mixture of a dimethylamine (DMA) salt of 2,4-dichlorophenoxy acetic acid (2,4-D) with a dimethylethanolamine (DMEA) salt or a diethylethanolamine (DEEA) salt of 2,4-D or a mixture thereof in a relative ratio of 2,4-D DMA salt to 2,4-D DMEA or DEEA salt of between about 55:45 to about 40:60, wherein the formulation contains at least 625 gram acid equivalents per liter (gae/L) to about 740 gae/L based upon the 2,4-D acid equivalent of the 2,4-D salt mixture.

2. The formulation of claim 1 wherein the 2,4-D DMEA or DEEA salt is the DMEA salt.

3. The formulation of claim 1 or 2 wherein the formulation contains about 710 gram acid equivalents per liter (gae/L) to about 725 gae/L based upon the 2,4-D acid equivalent of the 2,4-D salt mixture.

\* \* \* \* \*